US009768082B2

(12) United States Patent
Chou et al.

(10) Patent No.: US 9,768,082 B2
(45) Date of Patent: Sep. 19, 2017

(54) METHOD AND MACHINE FOR EXAMINING WAFERS

(75) Inventors: Chien-Hung Chou, San Jose, CA (US); Wen-Tin Tai, Fremont, CA (US)

(73) Assignee: HERMES MICROVISION INC., Hsinchu (TW)

( * ) Notice: Subject to any disclaimer, the term of this patent is extended or adjusted under 35 U.S.C. 154(b) by 0 days.

(21) Appl. No.: 13/589,378

(22) Filed: Aug. 20, 2012

(65) Prior Publication Data

US 2012/0314054 A1    Dec. 13, 2012

Related U.S. Application Data

(63) Continuation-in-part of application No. 12/370,913, filed on Feb. 13, 2009, now abandoned.

(51) Int. Cl.
| | |
|---|---|
| *G06F 19/00* | (2011.01) |
| *H01L 21/66* | (2006.01) |
| *G05B 19/418* | (2006.01) |
| *G01N 21/95* | (2006.01) |
| *G01N 21/88* | (2006.01) |

(52) U.S. Cl.
CPC ......... *H01L 22/20* (2013.01); *G01N 21/9501* (2013.01); *G05B 19/41875* (2013.01); *G01N 2021/8861* (2013.01); *G01N 2021/8867* (2013.01); *G05B 2219/32205* (2013.01); *G05B 2219/37224* (2013.01); *Y02P 90/20* (2015.11); *Y02P 90/22* (2015.11)

(58) Field of Classification Search
CPC .............. G05B 19/18; G05B 19/41875; G05B 19/41865; G05B 2219/312; H01L 21/67242; H01L 21/681; G01N 21/956; G01N 21/95607; G01N 2021/8854; G01N 2021/8861; G01N 2021/8864; G06T 7/0002; G06T 7/0006; H01J 2237/2817
USPC .......................................... 700/121; 382/149
See application file for complete search history.

(56) References Cited

U.S. PATENT DOCUMENTS

| | | | |
|---|---|---|---|
| 6,091,249 A * | 7/2000 | Talbot et al. ............. | 324/754.22 |
| 6,246,787 B1 * | 6/2001 | Hennessey ....... | G01N 21/95607 |
| | | | 250/559.45 |
| 6,336,086 B1 * | 1/2002 | Perez et al. ..................... | 703/13 |
| 6,363,382 B1 * | 3/2002 | Kotani et al. | |

(Continued)

FOREIGN PATENT DOCUMENTS

| | | |
|---|---|---|
| TW | 543081 | 7/2003 |
| TW | 200416504 | 9/2004 |
| TW | 200842341 | 11/2008 |

OTHER PUBLICATIONS

Taiwan Intellectual Property Office, "Office Action" issued Dec. 10, 2015.

*Primary Examiner* — Darrin Dunn
(74) *Attorney, Agent, or Firm* — Finnegan, Henderson, Farabow, Garrett & Dunner LLP

(57) ABSTRACT

Method and machine utilizes the real-time recipe to perform weak point inspection on a series of wafers during the fabrication of integrated circuits. Each real-time recipe essentially corresponds to a practical fabrication history of a wafer to be examined and/or the examination results of at least one examined wafer of same "lot". Therefore, different wafers can be examined by using different recipes where each recipe corresponds to a specific condition of a wafer to be examined, even these wafers are received by a machine for examining at the same time.

10 Claims, 4 Drawing Sheets

(56) References Cited

U.S. PATENT DOCUMENTS

| | | | |
|---|---|---|---|
| 6,449,524 B1* | 9/2002 | Miller et al. | 700/121 |
| 6,509,750 B1* | 1/2003 | Talbot et al. | 324/754.22 |
| 6,535,774 B1* | 3/2003 | Bode et al. | 700/109 |
| 6,724,929 B1* | 4/2004 | Matsuoka | 382/145 |
| 6,738,682 B1* | 5/2004 | Pasadyn | 700/100 |
| 6,830,941 B1* | 12/2004 | Lee et al. | 438/14 |
| 6,869,807 B2* | 3/2005 | Yoshitake et al. | 438/7 |
| 6,917,849 B1* | 7/2005 | Pasadyn et al. | 700/121 |
| 6,957,120 B1* | 10/2005 | Bode et al. | 700/121 |
| 6,980,687 B2* | 12/2005 | Ikegaya et al. | 382/149 |
| 7,142,992 B1* | 11/2006 | Huet | G01R 31/2846 702/58 |
| 7,248,939 B1* | 7/2007 | Chamness et al. | 700/121 |
| 7,310,585 B2* | 12/2007 | Brodsky | H01L 22/20 257/E21.525 |
| 7,313,450 B1* | 12/2007 | Fu et al. | 700/31 |
| 7,327,444 B2* | 2/2008 | Naka et al. | 356/73 |
| 7,327,475 B1* | 2/2008 | Chu et al. | 356/625 |
| 7,369,236 B1* | 5/2008 | Sali | G01N 21/95607 356/237.1 |
| 7,619,731 B2* | 11/2009 | Lally et al. | 356/237.5 |
| 7,636,649 B2* | 12/2009 | Li et al. | 702/188 |
| 7,676,077 B2* | 3/2010 | Kulkarni | G06F 17/5045 382/144 |
| 7,747,062 B2* | 6/2010 | Chen | G01N 21/8851 382/141 |
| 7,853,920 B2* | 12/2010 | Preil | G03F 1/84 382/149 |
| 7,877,722 B2* | 1/2011 | Duffy | G03F 7/7065 716/55 |
| 7,881,520 B2* | 2/2011 | Ueno | G01N 21/9501 356/237.2 |
| 7,906,758 B2* | 3/2011 | Stults et al. | 250/282 |
| 7,960,697 B2 | 6/2011 | Chen et al. | |
| 8,000,922 B2* | 8/2011 | Chen | G01N 21/9501 356/237.4 |
| 8,026,481 B2* | 9/2011 | Fukuda | H01J 37/263 250/306 |
| 8,041,103 B2* | 10/2011 | Kulkarni | G06F 17/5045 382/144 |
| 8,135,204 B1* | 3/2012 | Chen | G01N 21/9501 250/310 |
| 8,611,639 B2* | 12/2013 | Kulkarni | G01N 21/9501 382/145 |
| 2003/0121022 A1* | 6/2003 | Yoshitake et al. | 716/21 |
| 2003/0149506 A1* | 8/2003 | Haanstra et al. | 700/121 |
| 2004/0001619 A1* | 1/2004 | Tai | G06Q 10/04 382/141 |
| 2004/0046125 A1* | 3/2004 | Chen | H01J 37/141 250/396 ML |
| 2004/0141640 A1* | 7/2004 | Lee et al. | 382/149 |
| 2004/0185583 A1* | 9/2004 | Tomoyasu et al. | 438/8 |
| 2004/0262290 A1* | 12/2004 | Haanstra et al. | 219/490 |
| 2004/0267399 A1* | 12/2004 | Funk | G05B 19/41875 700/121 |
| 2005/0033528 A1* | 2/2005 | Toth | G01N 21/9501 702/35 |
| 2006/0015206 A1* | 1/2006 | Funk et al. | 700/121 |
| 2006/0078189 A1* | 4/2006 | Hosoya | G06K 9/033 382/149 |
| 2006/0195218 A1* | 8/2006 | Yamashita et al. | 700/121 |
| 2006/0265145 A1* | 11/2006 | Huet | G01R 31/2846 702/35 |
| 2007/0019856 A1* | 1/2007 | Furman et al. | 382/141 |
| 2007/0019858 A1* | 1/2007 | Shimura | 382/149 |
| 2007/0041631 A1* | 2/2007 | Fushida et al. | 382/149 |
| 2007/0045536 A1* | 3/2007 | Nakasuji et al. | 250/310 |
| 2007/0067134 A1* | 3/2007 | Borowicz | G05B 19/41875 702/127 |
| 2007/0156379 A1* | 7/2007 | Kulkarni et al. | 703/14 |
| 2007/0269101 A1* | 11/2007 | Hiroi et al. | 382/149 |
| 2007/0288219 A1* | 12/2007 | Zafar | G03F 1/84 703/14 |
| 2007/0293968 A1* | 12/2007 | Fu et al. | 700/108 |
| 2008/0163140 A1* | 7/2008 | Fouquet | G03F 7/7065 700/110 |
| 2008/0204739 A1* | 8/2008 | Huet | G01N 21/8851 356/237.5 |
| 2008/0250384 A1* | 10/2008 | Duffy | G03F 7/7065 716/55 |
| 2008/0298670 A1* | 12/2008 | Nakagaki et al. | 382/149 |
| 2009/0058444 A1* | 3/2009 | McIntyre | 324/755 |
| 2009/0070644 A1* | 3/2009 | Markle et al. | 714/724 |
| 2009/0080759 A1* | 3/2009 | Bhaskar | G06T 7/001 382/141 |
| 2009/0093904 A1* | 4/2009 | Baseman et al. | 700/110 |
| 2009/0212213 A1* | 8/2009 | Nakasuji et al. | 250/310 |
| 2009/0297019 A1* | 12/2009 | Zafar et al. | 382/145 |
| 2009/0299681 A1* | 12/2009 | Chen | G01N 21/9501 702/123 |
| 2010/0119144 A1* | 5/2010 | Kulkarni et al. | 382/149 |
| 2010/0150429 A1* | 6/2010 | Jau | G01N 23/04 382/149 |
| 2010/0158346 A1* | 6/2010 | Fang et al. | 382/149 |
| 2010/0189339 A1* | 7/2010 | Amanullah et al. | 382/145 |
| 2011/0001820 A1* | 1/2011 | Sato | G01R 31/2831 348/125 |
| 2011/0286656 A1* | 11/2011 | Kulkarni et al. | 382/144 |
| 2011/0320149 A1* | 12/2011 | Lee | G01N 21/9501 702/83 |
| 2012/0019279 A1* | 1/2012 | Huang | G01R 31/2884 324/762.01 |
| 2012/0087569 A1* | 4/2012 | O'Dell | G01N 21/9501 382/149 |
| 2012/0245861 A1* | 9/2012 | Greene | H01L 22/12 702/40 |
| 2012/0314054 A1* | 12/2012 | Chou | G05B 19/41875 348/87 |
| 2013/0202187 A1* | 8/2013 | Goren et al. | 382/149 |

* cited by examiner

METHOD AND MACHINE FOR EXAMINING WAFERS

CROSS-REFERENCE TO RELATED APPLICATIONS

The present invention is a continuation in part of the patent application in title of "Method and Machine for Examining Wafers" with application Ser. No. 12/370,913 filed in Feb. 13, 2009, currently pending, all of which is incorporated herein by reference.

FIELD OF THE INVENTION

The present invention relates to a method for examining wafers, and more particularly, to a method of weak point inspection for improving manufacture yield in semiconductor industry by using a charged particle beam tool.

BACKGROUND OF THE INVENTION

An integrated circuit (also referred to as IC, chip, or microchip) is an electronic circuit manufactured by the patterned diffusion of trace elements into the surface of a thin substrate of semiconductor material. Additional materials are deposited and patterned to form interconnections between semiconductor devices.

ICs were made possible by experimental discoveries showing that semiconductor device could perform the functions of vacuum tubes and by mid-20$^{th}$-century technology advancements in semiconductor device fabrication. The integration of large numbers of tiny transistors into a small chip was an enormous improvement over the manual assembly of circuits using discrete electronic components. The integrated circuit's mass production capability, reliability, and building-block approach to circuit design ensured the rapid adoption of standardized ICs in place of designs using discrete transistors.

In the early days of integrated circuits, only a few transistors could be placed on a chip, as the scale used was large because of the contemporary technology, and manufacturing yields were low by today's standards. As the degree of integration was small, the design was done easily. Over time, millions and today billions, of transistors could be placed on one chip, to make a good design become a task to be planned thoroughly.

ICs have consistently migrated to smaller feature sizes over the years, allowing more circuitry to be packed on each chip. In general, as the feature size shrinks, almost everything improves—the cost per unit and the switching power consumption go down, while the speed goes up. However, ICs with nanometer-scale devices still incur their original problems, principal among which is leakage current, although these problems will likely be solved or at least ameliorated by the introduction of high-k dielectrics.

Semiconductor ICs are fabricated in a layer process which includes these key processes: deposition, patterning, removal, and modification of electrical properties.

Deposition is any process that grows, coats, or otherwise transfers a material onto the wafer. Available technologies comprising physical vapor deposition (PVD), chemical vapor deposition (CVD), electrochemical deposition (EPC), molecular beam epitaxy (MBE) and more recently, atomic layer deposition (ALD) among others.

Patterning covers the series of processes that shape or alter the existing shape of the deposited materials and is generally referred to as lithography. For example, in conventional lithography, the wafer is coated with a chemical called a photoresist. The photoresist is exposed by a stepper, a machine that focuses, aligns, and moves the mask, exposing select portions of the wafer to short wavelength electromagnetic radiation. The unexposed regions are washed away by a developer solution. After etching or other processing, the remaining photoresist can be removed by plasma ashing.

Removal processes are any that remove material from the wafer either in bulk or selectively and consist primarily of etch processes, either wet etching or dry etching. Chemical-mechanical planarization (CMP) is also a removal process used between levels.

Modification of electrical properties has historically comprising doping sources and drains of a transistor originally by diffusion furnaces and later by ion implantation. These doping processes are followed by furnace anneal or in advanced devices, by rapid thermal anneal (RTA) which serve to activate the implanted dopants. Modification of electrical properties now also extends to reduction of dielectric constant in low-k insulating materials via exposure to ultraviolet light in UV processing (UVP).

Modern chips have up to eleven metal levels produced in over 300 sequenced processing steps.

In order to achieve the setting yield, the yield management of a fab needs to monitor, classify, eliminate or avoid defects from all kind of processes. A wafer map analysis has been developed for detecting and classifying patterns or process signatures based on low-resolution (e.g., 0.5 μm/pixel) optical defect image distribution. As wafers exit a fabrication process, wafer map data is generated by an in-line defect detection workstation incorporating a microscopy or light-scattering system. The information in the wafer map consists of detected defect coordinates as well as process information such as step, layer, and product. The wafer map data may be combined across wafers to further view the evaluation of process signatures which may assist in diagnosing manufacturing problems.

As the feature size shrinks, ICs yield improvement by defect reduction becomes more and more important. A pre-analysis of signatures of a process or a structure with computer workstation starts with using graphical database system (GDS) to construct photomask far a die, then to utilize the computational lithography to numerically simulate, and to improve the performance (resolution and contrast) of cutting-edge photomasks. Next optical proximity correction (OPC) process is introduced in the modern semi con due tor manufacturing. The OPC uses computational methods to counteract the effects of diffraction related blurring and under-exposure by modifying on mask geometries with means:

Adjusting line-widths depending on the density of surrounding geometries (a trace surrounded by a large area will be over-exposed compared with the same trace surrounded by a dense pattern).

Adding "dog-bone" end caps to the end of lines to prevent line shortening.

Correcting for electron beam proximity effects.

The computer-aid pre-analysis will illustrate a possible defect distribution positions within the IC which is named "hot spots" to the ICs yield management.

As a part of the wafer map process, an off-line defect review station examines these hot spots with a high resolution microscope, e.g., a defect inspection/review tool comprising scanning electron microscope (SEM), and classifies the defect according to individual morphology, color, texture, and relationship to process or layer.

The defect inspection/review tool proceeds wafer inspection/review job according to a process instruction called a "recipe". A "recipe" is a set of operating instructions (a processing program) that educates a tool how the tool should perform the process. The recipe varies for each kind of machine, and even among different machine manufactures for the same kind of machine. For example, an etch system by Applied Materials of Santa Clara, Calif. may require a 10-minute reaction time with a certain flow of gases, while the reaction chamber is kept at a certain, elevated temperature. At the end of the 10-minute reaction time, the flow of reactive gases is gradually reduced and replaced with inert gases as the temperature is lowered. Another etch system by Lam Research of Fremont, Calif. may require a 15-minute reaction time, with a different mixture of gases and a different temperature. Other kinds of semiconductor processing equipment require vastly different recipes. These recipes can become quite complex and vary as process engineers attempt to tweak the process for desired electrical and manufacturing-yield results. Different semiconductor products may require different recipes or combinations of steps. A DRAM process may require lighter ion implant doses than a process for logic chips and different oxide thicknesses require different reaction time in the furnace.

The recipe for a defect inspection/review tool contains instructions such as (a) product information that record the current inspection is after what semiconductor process; (b) inspection parameters that set the inspection tool, detecting area; and (e) detecting parameters that instruct the tool what to do in the detecting area. As an SEM-based defect inspection/review tool provides images at high resolution (e.g., 0.01 μm/pixel), however, the throughput of a fully examined wafer (e.g., 24 hours/wafer) is away below the expectation (e.g., 1 wafer/hour).

The wafer map analysis illustrates defects distribution after processing, in which the defect clustering area on the wafer is called "weak points" of the wafer. In order to meet the throughput requirement, a recipe instructs the inspection/review tool to perform the inspection according to the weak points might be a solution.

The present invention provides a weak point inspection method performed by a charged particle beam inspection/review tool to meet the throughput requirement in semiconductor manufacturing.

SUMMARY OF THE INVENTION

A weak point inspection method is disclosed. The present invention utilize high resolution SEM with SORIL objective lens, smart review sampling filter, and universal defect identification unit to construct wafer map and perform weak point inspection of the wafer and/or the "lot" of wafers accordingly.

The weak point inspection method examine only the critical area of a wafer defined by a predetermined wafer map instead of the whole wafer to enhance inspection throughput.

The weak point inspection method updates the wafer map of a specific process or a specific device after each wafer has been examined through. Therefore the weak point algorithm of the present invention has self-learning ability.

The weak, point inspection method may construct the "lot" own wafer map if no previous hot spot information can be referred to.

A machine to perform weak point inspection of wafers is equipped with a high resolution SORIL objective lens. The machine also is equipped with a smart review sampling filter to confine inspection area defined by wafer map, the universal defect identification unit to identify and classify defects.

DETAILED DESCRIPTION OF THE INVENTION

Reference will now be made in detail to specific embodiments of the invention. Examples of these embodiments are illustrated in accompanying drawings. While the invention will be described in conjunction with these specific embodiments, it will be understood that it is not Intended to limit the invention to these embodiments. On the contrary, it is intended to cover alternatives, modifications, and equivalents as may be included, within the spirit and scope of the invention as defined by the appended claims. In the following description, numerous specific details are set forth in order to provide a through understanding of the present invention. The present invention may be practiced without some or all of these specific details. In other instances, well known process operations are not described in detail in order not to unnecessarily obscure the present invention.

Terminology definition:
In the present invention "examine a wafer" implies the wafer is inspected by a charged particle beam system after the wafer experienced a semiconductor fabrication process in a process tool.
In the present invention "a "lot" of wafer" implies a group of semiconductor wafers that will experience a semiconductor fabrication process with a same process tool as a batch or one wafer at a time. The number of wafers within "a lot" maybe one or several wafers in a wafer cassette, or more than one cassette. Typically, one cassette may contain at most 25 200-mm wafers or 13 300-mm wafers.
In the present invention "hot spot" of a wafer of a semiconductor process implies a possible defect location within a die or a device provided by a prediction of a numerical simulation, a verified result of a previous inspection output of other defect scanning tool (e.g., a klarf file), and a historical wafer map result collected from previous wafers which experienced all fabrication processes.
In the present invention "weak point" of a wafer implies a defect clustering area which is illustrated through wafer map analysis.
in the present, invention a scanning electron microscope (SEM) will be use as an example to express a charged particle beam system.

Wafer inspection tools help semiconductor manufacturer increase and maintain ICs yield. The IC industry employs inspection tools to detect defects that occur during the fabrication process. The important characteristics of an inspection tool are defect detection sensitivity and wafer throughput. Sensitivity to detect a defect and wafer throughput are coupled such that greater sensitivity usually means lower throughput.

Figure 1:
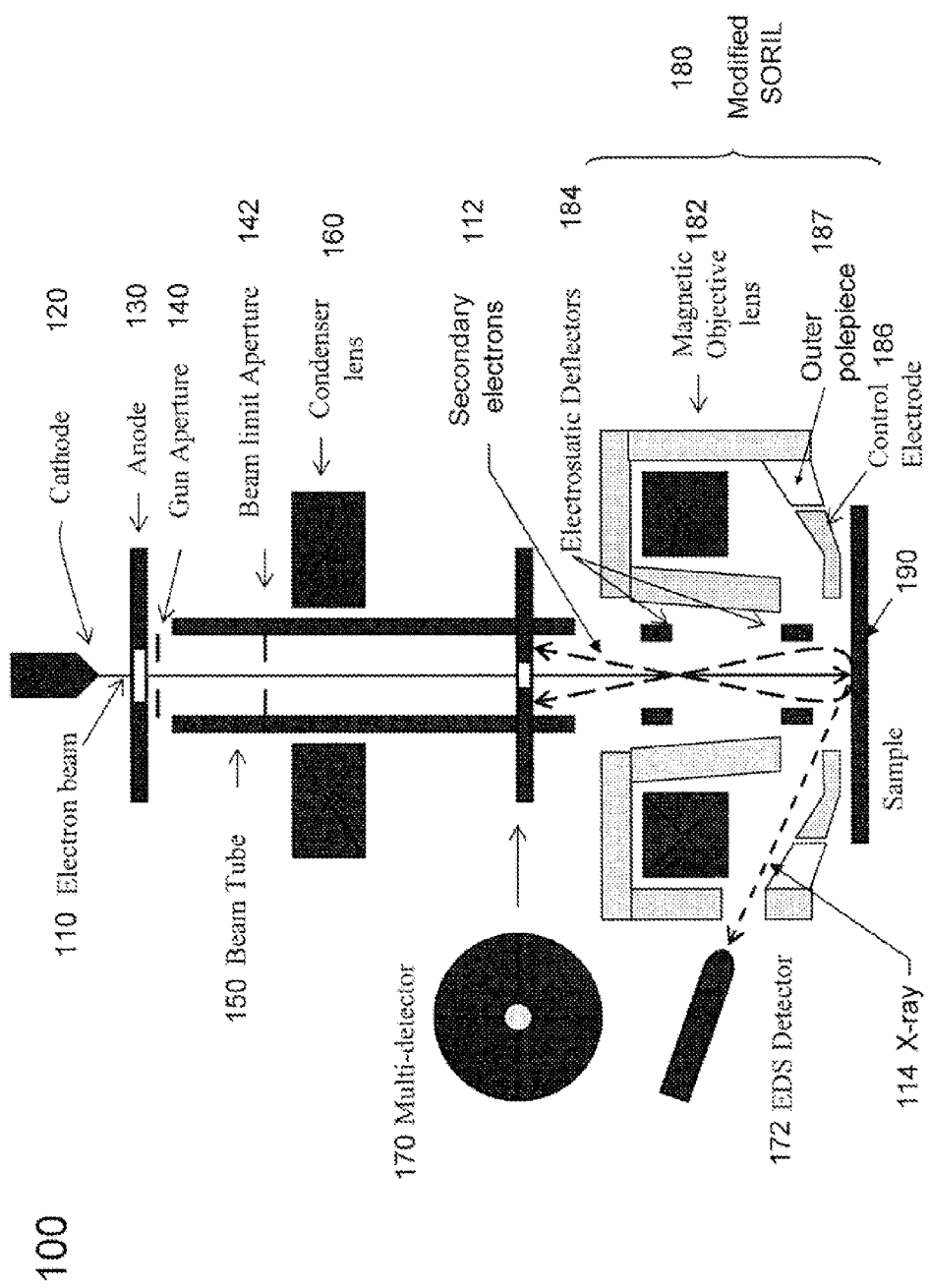
FIG. 1 is a schematic diagram illustration of a prior art imaging unit.

An scanning electron microscope (SEM) based inspection tool, for example, has an inspection probe spot diameter of 100 nm and a pixel rate of 12.5 million pixels per sec (Mpps), has a throughput of 0.05 300-mm wafers per hour (wph). A throughput at this level can not bear to do a full wafer inspection after a fabrication process. In order to perform valuable tool time to inspect critical position, a "hot spot" inspection and or a "weak point" inspection with a high resolution charged particle beam inspection tool is developed. FIG. 1 illustrates a SEM-based high resolution defect inspection/review tool with a swing objective retarding immersion lens (SORIL) developed by Chen et al. (U.S. Pat. No. 7,960,697), all of which is incorporated herein by reference. The beam tube 150 and the immersion magnetic field objective lens 182 provide high image resolution imaging unit for the present invention. The EDS detector 172 added to the modified SORIL 180 also provides an ability of identifying composition of defects.

U.S. patent application Ser. No. 13/303,953 in titled of "Smart Defect Review for Semiconductor Integrated Circuit" by Wang et al., filed in Nov. 23, 2011, all of which is incorporated herein by reference. As shown in FIG. 200, the present invention adopted the smart sampling review filter 240 algorithm developed by Wang et al. to set up a defect inspection or defect review plan, which instruct the inspection/review tool to locate defects from a confined area instead of the whole wafer based on previous loaded information. The present invention also adopted the universal defect identification unit 250 algorithm to identify defects through image comparison developed by Wang, et al.

Hot spot information of a specific semiconductor fabrication process with a specific processing tool maybe come from numerical simulation, wafer map analysis, and output file from other defect scanning tool. A "recipe" is constructed for a SEM-base defect inspection/review tool to instruct the tool perform defect inspection/review on those "hot spot" positions, to examine the possible defect positions with high resolution, to classify the real defect according to the defect shape, size, physical characteristics, and fabrication process. A wafer "weak point" map illustrates real defect distribution can be constructed after perform wafer map analysis according to the output of SEM-based defect review. Base on the result of the defect inspection/review tool, a fab manager can recommend corrective actions to the corresponding process or processing tool thereafter improve the yield of the fabrication process.

Figure 2:
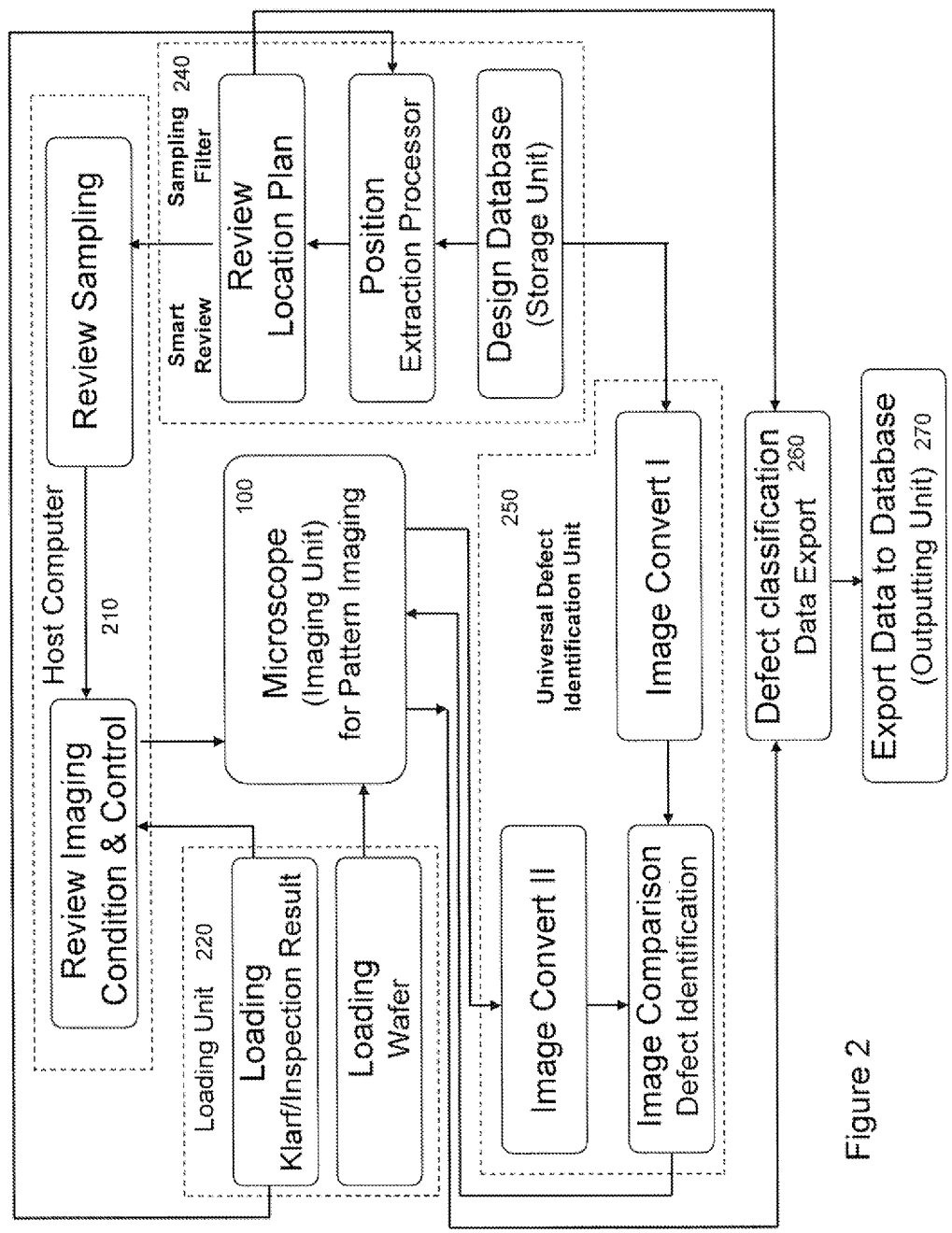
FIG. 2 is a schematic diagram illustration of a prior art defect finding algorism.
Figure 3:
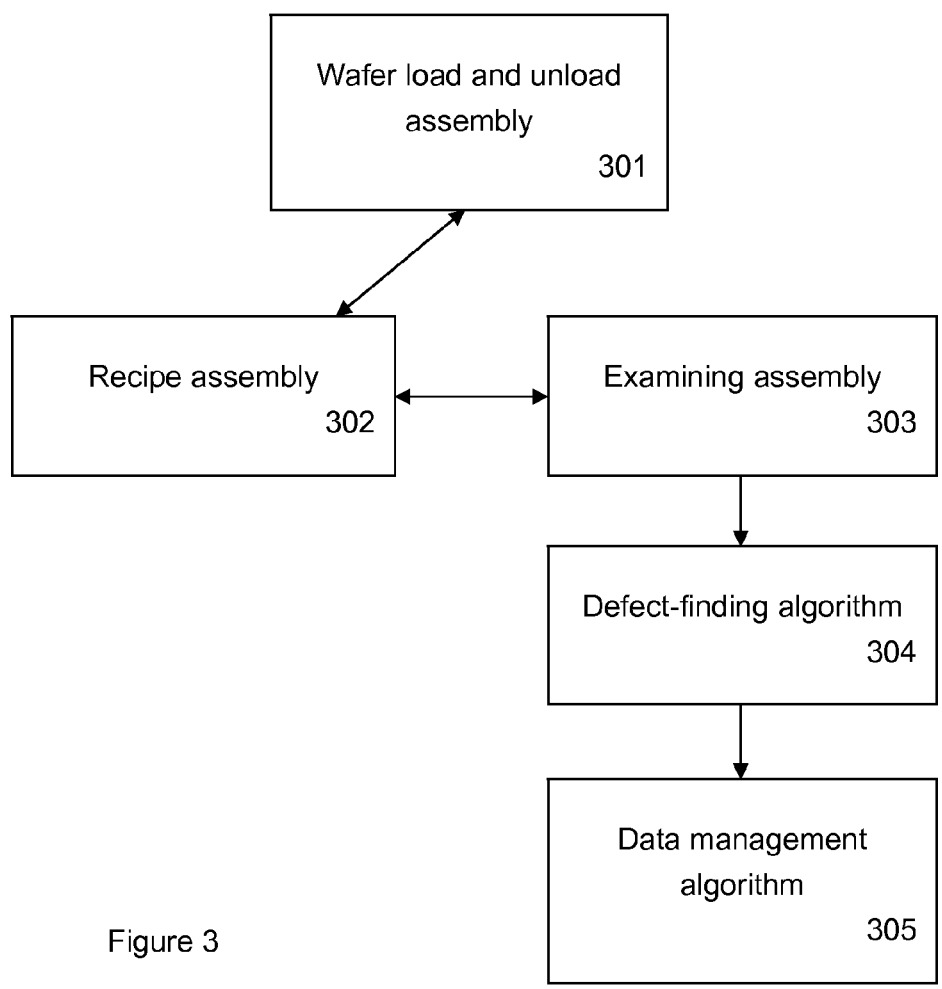
FIG. 3 is schematic diagram illustration of an inspection tool structure for examining wafers in accordance with an embodiment of present invention.

For a semiconductor fabrication process or processing tool that without previous experience to determine wafer "hot spot", one embodiment of the present invention to set up the inspection/review tool's own "weak point" map according to the inspection/review result of previous wafers. FIG. 3 illustrates a block diagram describing the key composition of the tool that performs weak point inspection in the present invention. Block 301 the wafer load and unload assembly which consists with the loading unit 220 of FIG. 2; block 302 the recipe assembly which consists with the smart review sampling filter 240 of FIG. 2; block 303 the examining assembly which consists with the imaging unit 100 of FIG. 2; block 304 the defect-finding algorithm which consists with the universal defect identification unit 250 of FIG. 2; block 305 the data management algorithm which consists with the combination of two function block data classification 260 and data export 270 of FIG. 2. A wafer map regarding defect distribution is constructed at the block 305.

Figure 4:
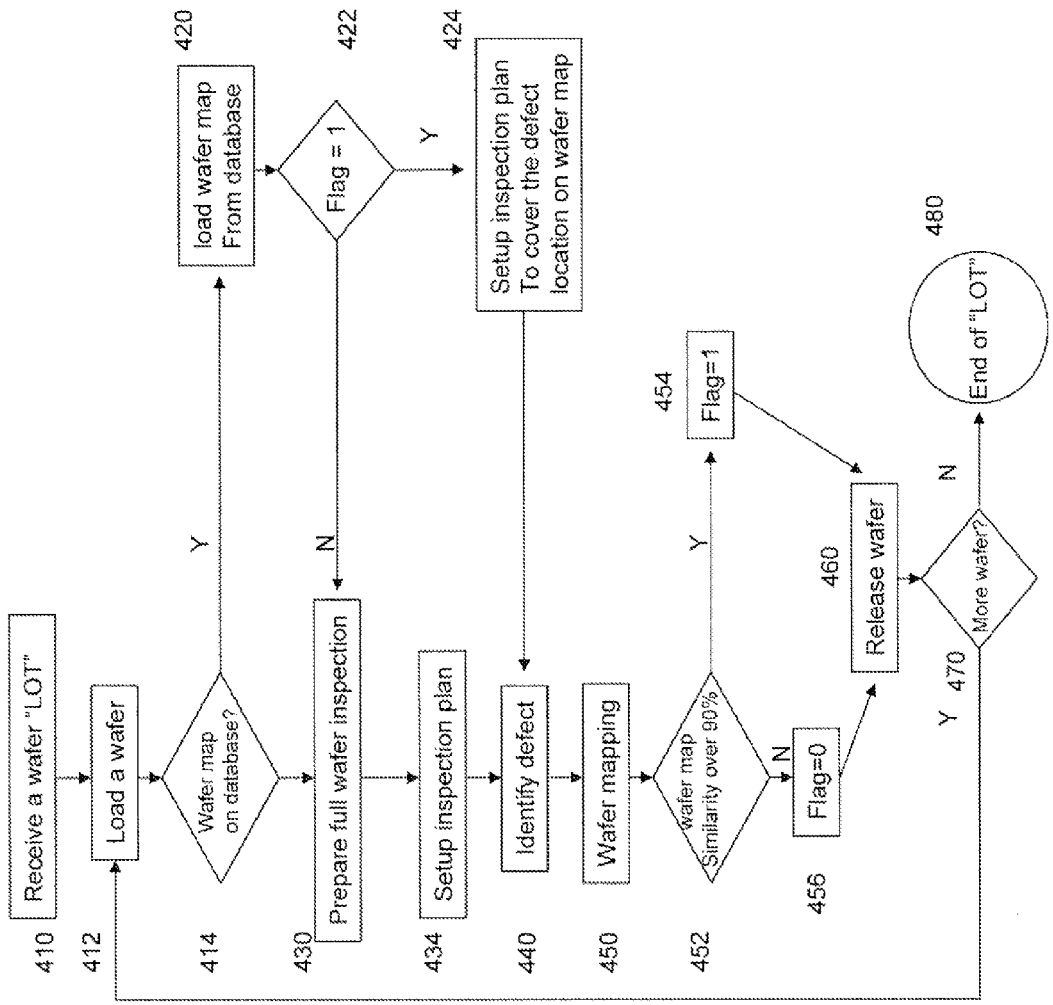
FIG. 4 is a schematic diagram illustration of a flowchart to perform weak point inspection in accordance with an embodiment of present invention.

FIG. 4 illustrates a flowchart to perform the self "weak point" inspection according to one embodiment of the present invention. A "lot" of wafers is sent to the defect inspection/review tool 100 (will be refer as tool 100 here since) and a wafer is loaded. The recipe will check if a wafer map already exists in database regarding the loaded wafer. If the answer is no, the wafer is undergoing a full wafer inspection, a full wafer inspection plan is setup accordingly as the step 430 and 434 illustrated in FIG. 4. If the answer is yes, the wafer map is loaded from database and a "weak point" inspection plan is setup to cover the defect located area according to the wafer map indicates (step 420, and step 424). The step 422 is for checking if the information of wafer map can represent the incoming wafer or not. If the answer is no, the recipe will back to step 430 and perform a full inspection for the loaded wafer. If the answer is yes then the recipe will perform step 424 to set up an inspection plan only to cover the critical area that indicates by the wafer map.

The tool 100 will identify defects in step 440 using algorithm of the universal defect locating unit 250. There are several methods can be chosen for defect identification. Three points comparison method, the method identify defects by comparing Images acquired from three different positions and mark error (defect) on the one deviate from the other two images. Die to golden die, the method identify defects by comparing images acquired from one die of the loaded wafer and a golden die to distinguish if a defect exists, where the golden die is refer to a perfect die without any defects. Die to design database or die to database, the method identify defects by comparing images acquired from a layout for a die or device of the loaded wafer and the original layout for a die or device on the design database.

The following step 450 is wafer mapping, this step records defects and its die/wafer location to database. The defect classification information such as defect type, size of the defect, composition of the defect if applied, process history of the wafer, coordinates on the wafer, location of the die (local coordinates), and etc., are recorded. After wafer mapping, the tool 100 compares found defects' position on the current wafer map and the previous wafer map. If the defects' position consistency is over 90% then set flag=1. Flag=1 indicates that the wafer map can pretty much represent the defect clustering area of a wafer in this "lot" and a weak point inspection plan setup according to this wafer map may cover most of the defect clustering area. If the defects position consistency is less than 90% then set flag=0. Flag=0 indicates next wafer will perform full wafer inspection again to accumulate defect distribution information. The tool 100 utilizes the smart review sampling algorithm 240 to construct the weak point inspection plan to save inspection time when Flag is set to 1.

Step 460 releases the wafer after inspection and in step 470 the recipe will request next wafer within the "lot" If there is any, the recipe will end the batch job in step 480 if no more wafer need to be inspected within the "lot".

It is because the information of the new discovered defect within the specified area will be updated to the wafer map database, therefore the weak point algorithm of the present invention has self-learning ability. Since the inspecting area of the next wafer loaded is varied according to the previous inspection results, in another word, the recipe of the inspection is varied in each inspection process.

The first advantage of the present invention is increasing throughput by focusing inspect ion area on critical or weak point area on the wafer. The second advantage of the present invention is that knowledge learned will accumulate automatically onto the database.

Although the present invention has been explained in relation to its preferred embodiment, it is to be understood that other modifications and variation can be made without departing the spirit and scope of the invention as hereafter claimed.

What is claimed is:

1. A method for performing wafer weak point inspection, comprising:
   receiving a lot including a first wafer and a second wafer;
   constructing a first inspecting plan for inspecting said first wafer according to a first defect wafer map from a database when said database contains said first defect wafer map and a wafer map flag is a first value, otherwise constructing said first inspecting plan according to a full wafer inspection, wherein said first inspecting plan covers only defect inspection area indicated by said first defect wafer map from said database;
   obtaining a first image of said first wafer with a high resolution imaging tool;
   identifying defects in said defect inspection area according to said first image;
   constructing a second defect wafer map based on said defect and recording said second defect wafer map into said database;
   setting said wafer map flag value to said first value when similarity between said first defect wafer map and said second defect wafer map exceeds a threshold, otherwise setting said wafer map flag value to a second value; and
   constructing a second inspecting plan for inspecting said second wafer according to said second defect wafer map from said database when said wafer map flag is said first value, otherwise constructing said second inspecting plan according to said full wafer inspection.

2. The method as claimed in claim 1, wherein said first inspecting plan is constructed by a smart review sampling filter.

3. The method as claimed in claim 1, wherein said high resolution imaging tool contains a swing objective retarding immersion lens (SORIL) objective lens.

4. The method as claimed in claim 1, wherein said defect is identified by a universal defect identification unit.

5. The method as claimed in claim 1, wherein said first defect wafer map comprises at least one of the following:
   a possible defect location within a die or a device provided by a prediction of a numerical simulation;
   a verified result of a previous inspection output of other defect scanning tool; and
   a historical wafer map result collected from said previous wafer which experienced all fabrication processes.

6. A machine for performing wafer weak point inspection; comprising:
   a load and unload assembly for receiving a lot including a first wafer and a second wafer;
   a recipe assembly for constructing a first inspecting plan for inspecting said first wafer according to a first defect wafer map from a database when said database contains said first defect wafer map and a wafer map flag is a first value, otherwise constructing said first inspecting plan according to a full wafer inspection, wherein said first inspecting plan covers only defect inspection area indicated by said first defect wafer map from the database;
   an examining assembly for obtaining a first image of said first wafer with a high resolution imaging tool;
   a defect finding algorism for identifying defects in said inspection area according to said first image; and
   a data management algorism constructing a second defect wafer map based on said defect and recording said second defect wafer map in said database, and setting said wafer map flag value to said first value when similarity between said first defect wafer map and said second defect wafer map exceeds a threshold, otherwise setting said wafer map flag value to a second value;
   wherein said recipe assembly constructs a second inspecting plan for inspecting said second wafer according to said second defect wafer map from said database when said wafer map flag is said first value, otherwise constructs said second inspecting plan according to said full wafer inspection.

7. The machine as claimed in claim 6, wherein said first inspecting plan assembly contains a smart review sampling filter.

8. The machine as claimed in claim 6, wherein said high resolution imaging tool contains a swing objective retarding immersion lens (SORIL) objective lens.

9. The machine as claimed in claim 6, wherein said defect finding algorism is a universal defect identification unit.

10. The machine as claimed in claim 6, wherein said first defect wafer map comprises at least one of the following:
    a possible defect location within a die or a device provided by a prediction of a numerical simulation;
    a verified result of a previous inspection output of other defect scanning tool; and
    a historical wafer map result collected from said previous wafer which experienced all fabrication processes.

* * * * *